(12) United States Patent
Collins

(10) Patent No.: US 8,353,893 B2
(45) Date of Patent: Jan. 15, 2013

(54) SYSTEM AND METHOD FOR RAPIDLY COOLING CARDIAC ARREST PATIENT

(75) Inventor: Kenneth A. Collins, Mission Viejo, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 1192 days.

(21) Appl. No.: 11/715,102

(22) Filed: Mar. 7, 2007

(65) Prior Publication Data

US 2008/0221553 A1    Sep. 11, 2008

(51) Int. Cl.
*A61M 25/10*    (2006.01)

(52) U.S. Cl. ........................................ 604/509; 604/510

(58) Field of Classification Search .................. 604/509, 604/508, 133, 113, 105, 510; 607/105
See application file for complete search history.

(56) References Cited

U.S. PATENT DOCUMENTS

| | | | | |
|---|---|---|---|---|
| 7,356 A * | 5/1850 | Atwood | ........................... | 126/77 |
| 62,961 A * | 3/1867 | Keyser | ........................... | 126/58 |
| 76,315 A * | 4/1868 | Evard | ........................... | 126/1 AE |
| 111,129 A * | 1/1871 | Macauley | ........................ | 112/234 |
| 114,614 A * | 5/1871 | Smith | .............................. | 126/98 |
| 117,129 A * | 7/1871 | Walker | ............................. | 454/36 |
| 123,142 A * | 1/1872 | Beckwith | ......................... | 126/58 |
| 127,535 A * | 6/1872 | Whittingham | .................. | 126/98 |
| 135,631 A * | 2/1873 | Corser | ........................ | 241/300.1 |
| 164,166 A * | 6/1875 | Gordon | .......................... | 426/624 |
| 171,129 A * | 12/1875 | Hermance | ....................... | 254/25 |
| 206,074 A * | 7/1878 | Beckwith | .................. | 126/152 R |
| 5,207,640 A | 5/1993 | Hattler | ............................. | 604/28 |
| 5,230,862 A | 7/1993 | Berry et al. | ..................... | 422/48 |
| 5,269,758 A * | 12/1993 | Taheri | ........................ | 604/96.01 |
| 5,271,743 A | 12/1993 | Hattler | ............................. | 604/26 |
| 5,279,598 A * | 1/1994 | Sheaff | ........................... | 604/290 |
| 5,437,633 A * | 8/1995 | Manning | ....................... | 604/500 |
| 5,450,516 A | 9/1995 | Pasquali et al. | ............... | 385/115 |
| 5,470,659 A | 11/1995 | Baumgart et al. | ............. | 428/398 |
| 5,474,533 A * | 12/1995 | Ward et al. | ...................... | 604/26 |
| 5,478,309 A * | 12/1995 | Sweezer et al. | .............. | 604/6.14 |
| 5,678,570 A * | 10/1997 | Manning | ....................... | 128/897 |
| 5,725,949 A | 3/1998 | Pasquail et al. | ............... | 428/398 |
| 5,735,809 A | 4/1998 | Gorsuch | ....................... | 428/364 |
| 5,755,690 A | 5/1998 | Saab | ............................... | 604/96 |
| 5,769,812 A * | 6/1998 | Stevens et al. | ............... | 604/4.01 |
| 5,792,094 A * | 8/1998 | Stevens et al. | ............... | 604/4.01 |
| 5,837,003 A | 11/1998 | Ginsburg | ....................... | 607/106 |
| 5,876,667 A | 3/1999 | Gremel et al. | .................... | 604/4 |

(Continued)

OTHER PUBLICATIONS

Wilhelm Behringer et al., "Rapid Hypothermic Aortic Flush Can Achieve Survival without Brain Damage after 30 Minutes Cardiac Arrest in Dogs", Anesthesiology 2000; 93:1491-9.*

(Continued)

*Primary Examiner* — Kevin C Sirmons
*Assistant Examiner* — Michael J Anderson
(74) *Attorney, Agent, or Firm* — John L. Rogitz

(57) ABSTRACT

A combined occlusion/infusion catheter is placed in the aorta of a cardiac arrest patient to occlude the aorta at a location just above the renal arteries/celiac trunk while rapidly infusing a liter or more of cold saline into the aorta below the occlusion. This flushes white cells from the bowel (now placed into a state of hypothermic stasis) induces hypothermia in the whole body, with perfusion pressure of the cold fluid maximized to the brain.

16 Claims, 1 Drawing Sheet

U.S. PATENT DOCUMENTS

| | | | | |
|---|---|---|---|---|
| 5,879,329 | A | 3/1999 | Ginsburg | 604/93 |
| 5,916,193 | A * | 6/1999 | Stevens et al. | 604/509 |
| 5,989,238 | A | 11/1999 | Ginsburg | 604/93 |
| 6,004,289 | A | 12/1999 | Saab | 604/96 |
| 6,019,783 | A | 2/2000 | Philips | 607/105 |
| 6,042,559 | A * | 3/2000 | Dobak, III | 604/7 |
| 6,096,068 | A | 8/2000 | Dobak | 607/105 |
| 6,110,168 | A | 8/2000 | Ginsburg | 606/27 |
| 6,126,684 | A | 10/2000 | Gobin | 607/113 |
| 6,146,411 | A | 11/2000 | Noda | 607/105 |
| 6,149,670 | A * | 11/2000 | Worthen et al. | 607/3 |
| 6,149,673 | A | 11/2000 | Ginsburg | 607/96 |
| 6,149,676 | A | 11/2000 | Ginsburg | 607/106 |
| 6,149,677 | A * | 11/2000 | Dobak, III | 607/106 |
| 6,165,207 | A | 12/2000 | Balding | 607/105 |
| 6,224,624 | B1 | 5/2001 | Lasheras | 607/105 |
| 6,231,594 | B1 | 5/2001 | Dae | 607/96 |
| 6,231,595 | B1 | 5/2001 | Dobak | 607/106 |
| 6,235,048 | B1 | 5/2001 | Dobak | 607/104 |
| 6,238,428 | B1 | 5/2001 | Werneth | 607/105 |
| 6,245,095 | B1 * | 6/2001 | Dobak et al. | 607/105 |
| 6,251,129 | B1 | 6/2001 | Dobak | 607/105 |
| 6,251,130 | B1 | 6/2001 | Dobak | 607/105 |
| 6,254,626 | B1 | 7/2001 | Dobak | 607/105 |
| 6,264,679 | B1 | 7/2001 | Keller | 607/105 |
| 6,287,326 | B1 * | 9/2001 | Pecor | 607/105 |
| 6,290,717 | B1 * | 9/2001 | Philips | 607/113 |
| 6,299,599 | B1 * | 10/2001 | Pham et al. | 604/113 |
| 6,306,161 | B1 | 10/2001 | Ginsburg | 607/106 |
| 6,312,452 | B1 * | 11/2001 | Dobak et al. | 607/105 |
| 6,325,818 | B1 | 12/2001 | Werneth | 607/105 |
| 6,338,727 | B1 * | 1/2002 | Noda et al. | 604/113 |
| 6,364,899 | B1 | 4/2002 | Dobak | 607/113 |
| 6,368,304 | B1 | 4/2002 | Aliberto | 604/113 |
| 6,379,378 | B1 | 4/2002 | Werneth | 607/96 |
| 6,383,210 | B1 | 5/2002 | Magers et al. | 607/105 |
| 6,393,320 | B2 * | 5/2002 | Lasersohn et al. | 607/3 |
| 6,405,080 | B1 | 6/2002 | Lasersohn | 607/3 |
| 6,409,747 | B1 | 6/2002 | Gobin | 607/113 |
| 6,416,533 | B1 | 7/2002 | Gobin | 607/113 |
| 6,419,643 | B1 | 7/2002 | Shimada | 600/323 |
| 6,428,563 | B1 | 8/2002 | Keller | 607/105 |
| 6,432,124 | B1 | 8/2002 | Worthen | 607/105 |
| 6,436,130 | B1 | 8/2002 | Philips | 607/105 |
| 6,436,131 | B1 | 8/2002 | Ginsburg | 607/106 |
| 6,440,158 | B1 | 8/2002 | Saab | 604/105 |
| 6,447,474 | B1 | 9/2002 | Balding | 604/66 |
| 6,450,987 | B1 | 9/2002 | Kramer | 604/523 |
| 6,450,990 | B1 | 9/2002 | Walker | 604/113 |
| 6,451,004 | B1 * | 9/2002 | Peters | 604/509 |
| 6,451,045 | B1 | 9/2002 | Walker | 607/105 |
| 6,454,792 | B1 | 9/2002 | Noda | 607/105 |
| 6,454,793 | B1 | 9/2002 | Evans | 607/105 |
| 6,458,150 | B1 | 10/2002 | Evans | 607/105 |
| 6,460,544 | B1 | 10/2002 | Worthen | 607/105 |
| 6,464,716 | B1 | 10/2002 | Dobak | 607/105 |
| 6,468,296 | B1 | 10/2002 | Dobak | 607/105 |
| 6,471,717 | B1 | 10/2002 | Dobak | 607/105 |
| 6,475,231 | B2 | 11/2002 | Dobak | 607/105 |
| 6,478,811 | B1 | 11/2002 | Dobak | 607/105 |
| 6,478,812 | B2 | 11/2002 | Dobak | 607/105 |
| 6,482,226 | B1 | 11/2002 | Dobak | 607/104 |
| 6,491,039 | B1 | 12/2002 | Dobak | 128/898 |
| 6,491,716 | B2 | 12/2002 | Dobak | 607/105 |
| 6,494,903 | B2 | 12/2002 | Pecor | 607/105 |
| 6,497,721 | B2 | 12/2002 | Ginsburg | 607/106 |
| 6,516,224 | B2 * | 2/2003 | Lasersohn et al. | 607/3 |
| 6,520,933 | B1 | 2/2003 | Evans | 604/103.07 |
| 6,527,798 | B2 | 3/2003 | Ginsburg | 607/106 |
| 6,529,775 | B2 | 3/2003 | Whitebook | 607/100 |
| 6,530,946 | B1 | 3/2003 | Noda | 607/113 |
| 6,533,804 | B2 | 3/2003 | Dobak | 607/105 |
| 6,540,771 | B2 | 4/2003 | Dobak | 607/105 |
| 6,544,282 | B1 | 4/2003 | Dae | 607/105 |
| 6,551,349 | B2 | 4/2003 | Lasheras | 607/105 |
| 6,554,797 | B1 | 4/2003 | Worthen | 604/113 |
| 6,558,412 | B2 | 5/2003 | Dobak | 607/105 |
| 6,572,538 | B2 | 6/2003 | Takase | 600/140 |
| 6,572,638 | B1 | 6/2003 | Dae et al. | 607/96 |
| 6,572,640 | B1 | 6/2003 | Balding | 607/105 |
| 6,576,001 | B2 | 6/2003 | Werneth | 607/96 |
| 6,576,002 | B2 | 6/2003 | Dobak | 607/105 |
| 6,581,403 | B2 | 6/2003 | Whitebook | 62/434 |
| 6,582,398 | B1 | 6/2003 | Worthen | 604/113 |
| 6,582,455 | B1 | 6/2003 | Dobak | 607/105 |
| 6,582,457 | B2 | 6/2003 | Dae | 607/113 |
| 6,585,692 | B1 | 7/2003 | Worthen | 604/113 |
| 6,585,752 | B2 | 7/2003 | Dobak | 607/105 |
| 6,589,271 | B1 | 7/2003 | Tzeng | 607/113 |
| 6,595,967 | B2 | 7/2003 | Kramer | 604/523 |
| 6,599,312 | B2 | 7/2003 | Dobak | 607/105 |
| 6,602,243 | B2 | 8/2003 | Noda | 604/544 |
| 6,602,276 | B2 | 8/2003 | Dobak | 607/105 |
| 6,607,517 | B1 | 8/2003 | Dae | 604/31 |
| 6,610,083 | B2 | 8/2003 | Keller | 607/105 |
| 6,620,130 | B1 | 9/2003 | Ginsburg | 604/113 |
| 6,620,131 | B2 | 9/2003 | Pham | 604/113 |
| 6,620,188 | B1 | 9/2003 | Ginsburg | 607/106 |
| 6,620,189 | B1 | 9/2003 | MacHold et al. | 607/106 |
| 6,623,516 | B2 | 9/2003 | Saab | 607/105 |
| 6,635,076 | B1 | 10/2003 | Ginsburg | 607/106 |
| 6,641,602 | B2 | 11/2003 | Balding | 607/105 |
| 6,641,603 | B2 | 11/2003 | Walker | 607/105 |
| 6,645,234 | B2 * | 11/2003 | Evans et al. | 607/105 |
| 6,648,906 | B2 | 11/2003 | Lasheras | 607/105 |
| 6,648,908 | B2 | 11/2003 | Dobak | 607/105 |
| 6,652,565 | B1 | 11/2003 | Shimada | 607/113 |
| 6,656,209 | B1 | 12/2003 | Ginsburg | 607/106 |
| 6,660,028 | B2 | 12/2003 | Magers | 607/105 |
| 6,669,661 | B1 * | 12/2003 | Yee | 604/6.13 |
| 6,673,098 | B1 | 1/2004 | MacHold | 607/106 |
| 6,676,688 | B2 | 1/2004 | Dobak | 607/105 |
| 6,676,689 | B2 | 1/2004 | Dobak | 607/105 |
| 6,676,690 | B2 | 1/2004 | Werneth | 607/105 |
| 6,679,906 | B2 | 1/2004 | Hammack | 607/105 |
| 6,679,907 | B2 | 1/2004 | Dobak | 607/105 |
| 6,682,551 | B1 | 1/2004 | Worthen | 607/105 |
| 6,685,732 | B2 | 2/2004 | Kramer | 607/106 |
| 6,685,733 | B1 | 2/2004 | Dae | 607/105 |
| 6,692,488 | B2 | 2/2004 | Dobak | 606/21 |
| 6,692,519 | B1 | 2/2004 | Hayes | 607/105 |
| 6,695,873 | B2 | 2/2004 | Dobak | 607/105 |
| 6,695,874 | B2 | 2/2004 | MacHold | 607/106 |
| 6,699,268 | B2 | 3/2004 | Kordis | 607/113 |
| 6,702,783 | B1 | 3/2004 | Dae | 604/113 |
| 6,702,839 | B1 | 3/2004 | Dae | 607/96 |
| 6,702,840 | B2 | 3/2004 | Keller | 607/105 |
| 6,702,841 | B2 | 3/2004 | Nest | 607/105 |
| 6,702,842 | B2 | 3/2004 | Dobak | 607/105 |
| 6,706,060 | B2 | 3/2004 | Tzeng | 607/105 |
| 6,709,448 | B2 | 3/2004 | Walker | 607/105 |
| 6,716,188 | B2 | 4/2004 | Noda | 604/6.13 |
| 6,716,236 | B1 | 4/2004 | Tzeng | 607/113 |
| 6,719,723 | B2 | 4/2004 | Werneth | 604/113 |
| 6,719,724 | B1 | 4/2004 | Walker | 604/113 |
| 6,719,779 | B2 | 4/2004 | Daoud | 607/105 |
| 6,726,653 | B2 | 4/2004 | Noda | 604/113 |
| 6,726,708 | B2 | 4/2004 | Lasheras | 607/105 |
| 6,726,710 | B2 | 4/2004 | Worthen | 607/105 |
| 6,733,517 | B1 | 5/2004 | Collins | 607/105 |
| 6,740,109 | B2 | 5/2004 | Dobak | 607/105 |
| 6,749,585 | B2 | 6/2004 | Aliberto | 604/113 |
| 6,749,625 | B2 | 6/2004 | Pompa | 607/105 |
| 6,752,786 | B2 | 6/2004 | Callister | 604/113 |
| 6,755,850 | B2 | 6/2004 | Dobak | 607/104 |
| 6,755,851 | B2 | 6/2004 | Noda | 607/113 |
| 7,258,662 | B2 * | 8/2007 | Machold et al. | 600/104 |
| 7,311,725 | B2 * | 12/2007 | Dobak, III | 607/106 |
| 7,326,195 | B2 * | 2/2008 | Willard et al. | 604/508 |
| 2001/0001832 | A1 * | 5/2001 | Dobak et al. | 607/105 |
| 2001/0007951 | A1 | 7/2001 | Dobak | 607/105 |
| 2001/0016764 | A1 | 8/2001 | Dobak, III | 607/105 |
| 2001/0041923 | A1 | 11/2001 | Dobak | 607/105 |
| 2001/0047196 | A1 * | 11/2001 | Ginsburg et al. | 607/96 |
| 2001/0049545 | A1 * | 12/2001 | Lasersohn et al. | 607/106 |
| 2002/0002394 | A1 * | 1/2002 | Dobak, III | 607/106 |
| 2002/0007203 | A1 | 1/2002 | Gilmartin | 607/105 |

| | | | |
|---|---|---|---|
| 2002/0013569 A1* | 1/2002 | Sterman et al. | 604/508 |
| 2002/0016621 A1 | 2/2002 | Werneth | 607/96 |
| 2002/0029016 A1* | 3/2002 | Pham et al. | 604/101.05 |
| 2002/0032430 A1* | 3/2002 | Luo et al. | 604/512 |
| 2002/0068964 A1 | 6/2002 | Dobak | 607/113 |
| 2002/0077680 A1 | 6/2002 | Noda | 600/549 |
| 2002/0091429 A1 | 7/2002 | Dobak | 607/105 |
| 2002/0111616 A1 | 8/2002 | Dea | 606/27 |
| 2002/0151946 A1 | 10/2002 | Dobak, III | 607/105 |
| 2002/0177804 A1 | 11/2002 | Saab | 607/105 |
| 2002/0183692 A1 | 12/2002 | Callister | 604/113 |
| 2002/0193738 A1 | 12/2002 | Adzich | 604/113 |
| 2002/0193853 A1 | 12/2002 | Worthen | 607/3 |
| 2002/0193854 A1 | 12/2002 | Dobak, III et al. | 607/105 |
| 2003/0060762 A1* | 3/2003 | Zvuloni et al. | 604/113 |
| 2003/0078641 A1 | 4/2003 | Dobak, III | 607/105 |
| 2003/0114835 A1 | 6/2003 | Noda | 604/544 |
| 2003/0144714 A1 | 7/2003 | Dobak, III | 607/104 |
| 2003/0187489 A1 | 10/2003 | Dobak, III et al. | 607/105 |
| 2003/0195465 A1 | 10/2003 | Worthen | 604/113 |
| 2003/0195466 A1 | 10/2003 | Pham | 604/113 |
| 2003/0195597 A1 | 10/2003 | Keller | 607/105 |
| 2003/0216799 A1 | 11/2003 | Worthen | 606/27 |
| 2003/0225336 A1 | 12/2003 | Callister | 600/505 |
| 2003/0236496 A1* | 12/2003 | Samson et al. | 604/103.02 |
| 2004/0034399 A1 | 2/2004 | Ginsburg | 607/106 |
| 2004/0039431 A1 | 2/2004 | Machold | |
| 2004/0044388 A1 | 3/2004 | Pham | 607/105 |
| 2004/0050154 A1 | 3/2004 | Machold | |
| 2004/0054325 A1 | 3/2004 | Ginsburg | 604/113 |
| 2004/0073280 A1 | 4/2004 | Dae | |
| 2004/0087934 A1 | 5/2004 | Dobak, III et al. | |
| 2004/0102825 A1 | 5/2004 | Daoud | |
| 2004/0102826 A1 | 5/2004 | Lasheras et al. | |
| 2004/0102827 A1 | 5/2004 | Werneth | |
| 2004/0106969 A1 | 6/2004 | Dobak, III et al. | |
| 2004/0111138 A1 | 6/2004 | Bleam | 607/105 |
| 2004/0116987 A1 | 6/2004 | Magers et al. | |
| 2004/0116988 A1 | 6/2004 | Hammack | |
| 2004/0127851 A1 | 7/2004 | Noda | 604/503 |
| 2004/0143312 A1* | 7/2004 | Samson et al. | 607/105 |
| 2004/0147987 A1* | 7/2004 | Ginsburg et al. | 607/106 |
| 2004/0167467 A1* | 8/2004 | Harrison et al. | 604/113 |
| 2006/0036303 A1* | 2/2006 | Schwartz | 607/106 |
| 2006/0058859 A1* | 3/2006 | Merrill | 607/105 |
| 2006/0064146 A1 | 3/2006 | Collins | 607/105 |
| 2006/0095104 A1* | 5/2006 | Magers et al. | 607/105 |
| 2006/0200215 A1* | 9/2006 | Collins | 607/105 |
| 2006/0293732 A1* | 12/2006 | Collins et al. | 607/104 |
| 2007/0000278 A1* | 1/2007 | Collins et al. | 62/434 |
| 2007/0135793 A1* | 6/2007 | Barbut et al. | 604/509 |
| 2007/0239135 A9* | 10/2007 | Barbut | 604/507 |

OTHER PUBLICATIONS

U.S. Appl. No. 60/272,442, Worthen et al.

* cited by examiner

SYSTEM AND METHOD FOR RAPIDLY COOLING CARDIAC ARREST PATIENT

I. FIELD OF THE INVENTION

The present invention relates generally to systems and methods for rapidly cooling cardiac arrest patients.

II. BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia.

As understood herein it may be advantageous, particularly for cardiac arrest patients, to immediately and rapidly perfuse one or more critical organs with cold fluid. The present invention also understands that owing to the structure of the arterial system, it may be necessary to provide a means to maintain the cold fluid in a desired body location for at least a limited time. With these critical recognitions in mind, the invention herein is provided.

SUMMARY OF THE INVENTION

A method includes advancing a combined occlusion/infusion catheter into the aorta of a cardiac arrest patient and then using the catheter to occlude the aorta at a location just above the renal arteries/celiac trunk. The catheter is then used to infuse cold saline into the aorta below the occlusion.

In non-limiting implementations between one and four liters of cold saline are infused through the catheter into the aorta, preferably at a rate of approximately one liter per minute.

As set forth further below, in some implementations the catheter can include at least an upper balloon that is inflatable once inside the aorta to substantially completely occlude the aorta. Also, the catheter may include a lower balloon that can be inflated once inside the aorta to substantially completely occlude the aorta at a location just below the lower mesenteric artery. Preferably, the catheter is inserted and used as rapidly as possible after the cardiac arrest if the patient is comatose regardless of the state of spontaneous circulation in the patient.

In another aspect, a catheter system includes an elongated flexible body and at least an upper balloon on the body at or near a distal end thereof. An inflation lumen is formed in the body and communicates with the balloon to move the balloon from a deflated configuration, wherein the balloon can be advanced into the aorta of a patient above the renal arteries, to an inflated configuration, wherein the balloon is sufficiently large to substantially completely occlude the aorta above the renal arteries. An infusion lumen is also formed on the body and terminates at a port below the upper balloon. With this structure, a source of saline having a temperature of less than five degrees Centigrade can be placed in fluid communication with the infusion lumen and a source of inflation fluid can be placed in fluid communication with the inflation lumen.

In still another aspect, a catheter is advanced into a patient's aorta after the patient has suffered cardiac arrest regardless of the state of spontaneous circulation. The method below may also be used with non-arrest myocardial infarction patients. Regardless, an upper balloon in a deflated configuration is advanced to a location just above the renal arteries and celiac trunk and then inflated to occlude the lower aorta above the renal arteries and celiac trunk. With the aorta blocked by the upper balloon, cold biocompatible fluid is infused through the catheter into the aorta below the balloon, after which the balloon is deflated and the catheter withdrawn.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
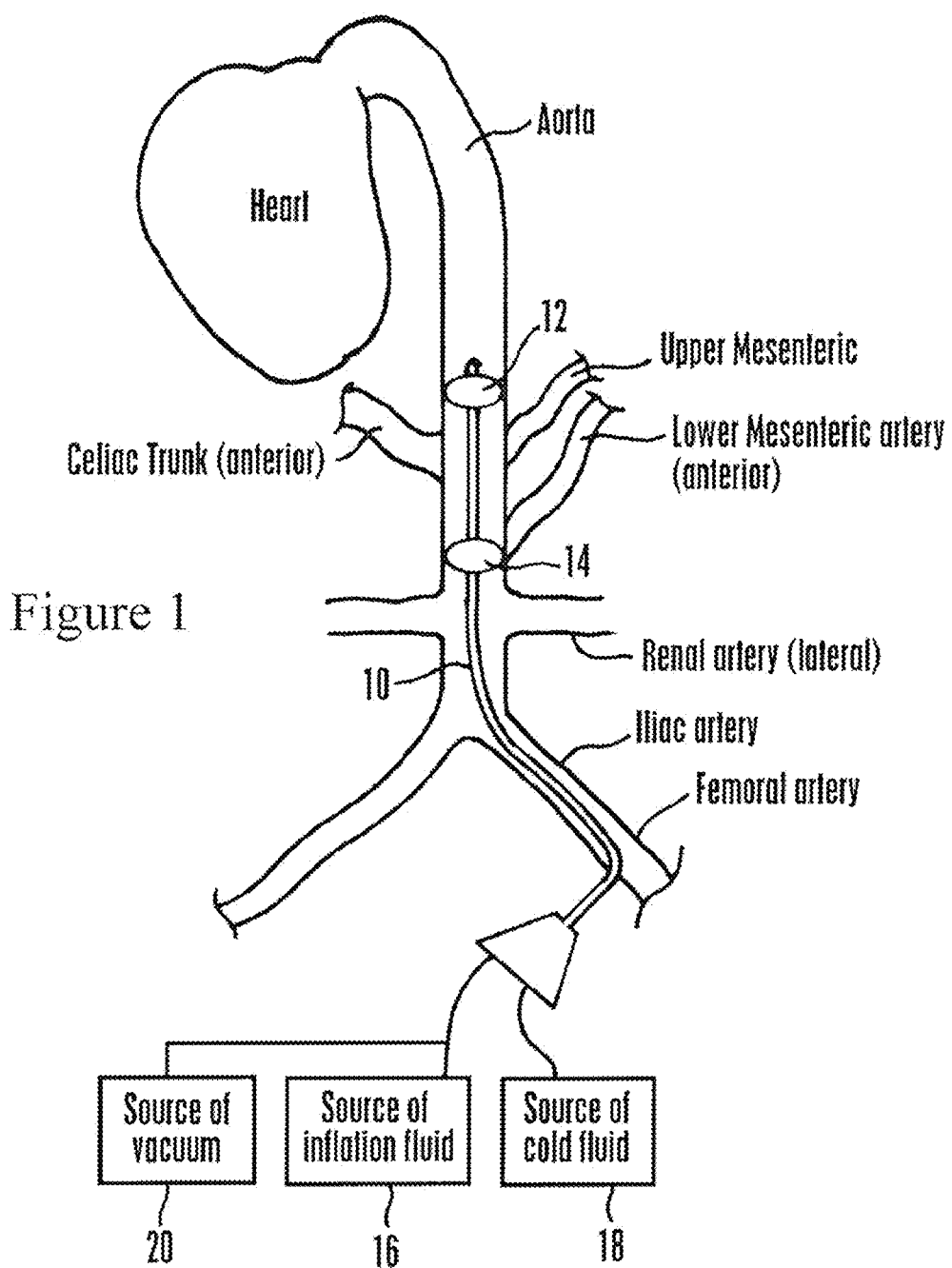
FIG. 1 is a schematic diagram showing a non-limiting catheter engaged with the arterial system of a patient immediately post-cardiac arrest.

Referring initially to FIG. 1, a catheter 10 is shown advanced into the arterial system of a patient who has suffered cardiac arrest. It is preferred that the catheter 10 is inserted and used as described below as rapidly as possible after the arrest if the patient is comatose regardless of the state of spontaneous circulation.

FIG. 1 labels relevant branches of the aorta of the patient to give perspective in the preferred placement of the catheter 10. An upper balloon 12 in a deflated configuration is advanced into the lower aorta to a location just above the renal arteries and celiac trunk as shown and then inflated to occlude, preferably completely, the lower aorta above the renal arteries and celiac trunk.

In non-limiting implementations the catheter 10 may further include a lower balloon 14 located on the catheter 10 (assuming a standard adult anatomy) to be disposed below the inferior mesenteric artery when the upper balloon 12 is positioned as described above. Thus, it is to be understood that the terms "upper" and "lower" are intended to convey the locations of the balloons with respect to each other relative to the patient's anatomy when the balloons are operatively disposed in the patient.

Once inflated, the lower balloon 14 thus occludes, preferably completely, flow of the cold fluid described below to the lower extremities and other organs below the level of the lower mesenteric artery thereby ensuring that the majority of the cold fluid flows through the enteric vascular bed. When a lower balloon 14 is not used, a higher volume of infused fluid than described below may be used.

As shown in FIG. 1, in non-limiting implementations the catheter 10 can be advanced into the location shown through a femoral artery, the associated iliac artery, and into and upward in the aorta. Other vessels may be used for insertion.

Once the upper balloon 12 (and if provided, the lower balloon 14) are positioned as shown in FIG. 1, the balloons are inflated with saline or other solution to fully occlude the aorta in the locations shown. The inflation fluid may be infused from a suitable inflation fluid source 16 that can have a pump.

Then, with the aorta blocked cold biocompatible fluid such as saline is infused through the catheter 10 to emerge at the below-described distal port of the catheter 10 into the aorta. The cold fluid may be infused from a source 18 of cold fluid that can include a pump. It is preferred that the infusion of the cold fluid is rapid, approximately one liter per minute or faster, and for a relatively short period of time, e.g., two to four minutes, for a total volume of between two to four liters of cold fluid. It is preferred that the infusion fluid be very cold, e.g., when saline is used the temperature of the saline may be less than ten degrees Centigrade, more preferably less than five degrees Centigrade, and more preferably still about one to two degrees Centigrade.

After infusing the cold fluid into the aorta, the balloon(s) 12, 14 are deflated and spontaneous circulation is resumed, assuming the heart has not already been brought out of arrest. To this end, a source 20 of vacuum may be connected to the same line through which inflation fluid was infused and actuated to rapidly deflate the balloons. The catheter 10 is then withdrawn from the body.

Figure 2:
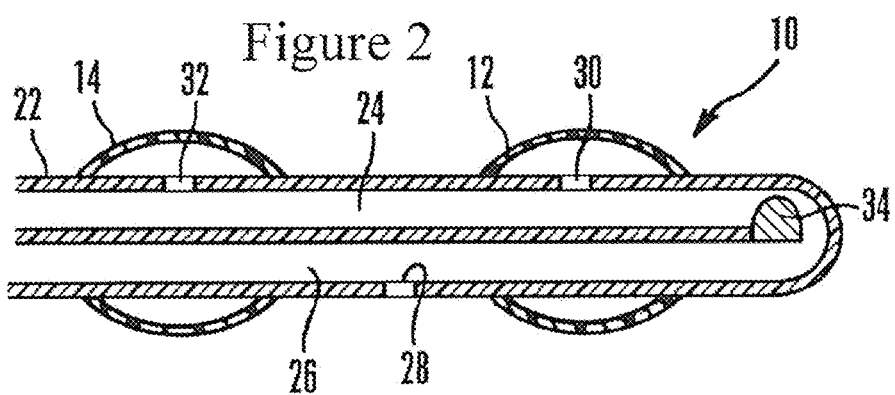
FIG. 2 is a cross-sectional diagram of the catheter shown in FIG. 1.

FIG. 2 shows additional details of the non-limiting catheter 10 shown in FIG. 1. The catheter 10 includes a flexible elongated plastic body 22 onto which the balloons 12, 14 may be, e.g., bonded. The body 22 can be formed with at least two lumens, and in the embodiment shown is formed with an inflation/deflation lumen 24 and an infusion lumen 26 that terminates in an infusion port 28 distal to the lower balloon 14 and proximal to the upper balloon 12 as shown (i.e., located axially between the balloons). It is to be understood that the source 16 of inflation fluid and the source 20 of vacuum shown in FIG. 1 are connected to the inflation/deflation lumen 24. On the other hand, the source 18 of cold fluid shown in FIG. 1 is connected to the infusion lumen 26, so that the cold fluid from the source 18 can flow through the infusion lumen 26 and exit the catheter 10 through the infusion port 28 into the aorta, below the upper balloon 12 and above the lower balloon 14 (and hence into the celiac artery, the upper mesenteric artery, and the lower mesenteric artery.

To provide a pathway for inflation fluid communication from the inflation/deflation lumen 24 in the body 22 to the interior of the balloons 12, 14, respective inflation/deflation ports 30, 32 are formed in the catheter body 22 as shown. The ports 30, 32 extend completely between the inflation/deflation lumen 24 and the interiors of the balloons 12, 14. More than one port per balloon may be used to promote rapid inflation and deflation.

If desired, within the catheter 10 at or near the axial location of the upper balloon 12 (e.g., at the distal tip of the catheter 10) an ultrasonic repeater 34 such as a crystal can be mounted by, e.g., bonding the repeater 34 to the body 22. In accordance with ultrasonic locating techniques known in the art, an ultrasound transponder (not shown) can be disposed on the skin of the patient immediately below the edge of the ribs and in the anterior midline. The transponder can be activated to transmit an ultrasonic pulse that has a maximized return immediately above the location of the repeater 34, and an indication of the maximized return can be presented to the surgeon. In this manner, the catheter 10 may be properly located above the visceral arteries.

The catheter 10 may be coated with biocompatible coatings (e.g., heparin) to reduce clotting and/or with antimicrobial coatings to reduce the risk of infection.

With the above disclosure in mind, it will now be appreciated that use of the catheter 10 as disclosed, owing to infusing cold saline into the arteries between the balloons 12, 14, acts to flush white cells from the bowel, as well as to place the bowel into a state of hypothermic stasis. At the same time, hypothermia induction in the whole body advantageously is commenced, with perfusion pressure of the cold fluid maximized to the brain.

While the particular SYSTEM AND METHOD FOR RAPIDLY COOLING CARDIAC ARREST PATIENT is herein shown and described in detail, it is to be understood that the subject matter which is encompassed by the present invention is limited only by the claims.

What is claimed is:

1. A method comprising:
advancing an occlusion/infusion catheter into the aorta of a cardiac arrest patient;
using the catheter to occlude the aorta at an anatomic location just above the renal arteries/celiac trunk; and
using the catheter to infuse cold saline into the aorta anatomically below the occlusion caused by the catheter.

2. The method of claim 1, comprising infusing between one and four liters of cold saline into the aorta.

3. The method of claim 2, comprising infusing the saline at a rate of approximately one liter per minute.

4. The method of claim 1, wherein the catheter includes at least an upper balloon inflatable once inside the aorta to substantially completely occlude the aorta.

5. The method of claim 1, wherein the catheter includes at least a lower balloon inflatable once inside the aorta to substantially completely occlude the aorta at a location just below the lower mesenteric artery.

6. The method of claim 1, wherein the catheter is inserted and used as rapidly as possible after the cardiac arrest if the patient is comatose regardless of the state of spontaneous circulation in the patient.

7. The method of claim 1, further comprising using ultrasound to locate the catheter.

8. A catheter system, comprising:
an elongated flexible body;
at least an upper balloon on the body at or near a distal end thereof;
at least one inflation lumen formed in the body and communicating with the balloon to move the balloon from a deflated configuration, wherein the balloon can be advanced into the aorta of a patient to a location that is anatomically above the renal arteries, to an inflated configuration, wherein the balloon is sufficiently large to substantially completely occlude the aorta above the renal arteries and below the heart;
at least one infusion lumen formed on the body and terminating at a port proximal to the upper balloon and anatomically below the balloon when the balloon is inflated and positioned above the renal arteries and below the heart;
a source of saline having a temperature of less than five degrees Centigrade and communicating with the infusion lumen; and
a source of inflation fluid communicating with the inflation lumen.

9. The system of claim 8, further comprising a source of vacuum communicating with the inflation lumen to move the balloon from the inflated to the deflated configuration.

10. The system of claim 8, further comprising a lower balloon on the body and movable between a deflated configuration, wherein the lower balloon can be advanced into the aorta of a patient to a position just below the lower mesenteric artery, and an inflated configuration, wherein the lower balloon is sufficiently large to substantially completely occlude the aorta just below the lower mesenteric artery, the port being formed between the balloons.

11. The system of claim 8, further comprising an ultrasonic repeater located on the catheter body adjacent the balloon.

12. A method, comprising:
advancing a catheter into a patient's aorta after the patient has suffered cardiac arrest regardless of the state of spontaneous circulation;

positioning an upper balloon while in a deflated configuration to a location just above the renal arteries and celiac trunk;

inflating the upper balloon to occlude the lower aorta above the renal arteries and celiac trunk;

with the aorta blocked by the upper balloon, infusing cold biocompatible fluid through the catheter into the aorta anatomically below the upper balloon;

deflating the balloon; and withdrawing the catheter from the patient.

13. The method of claim 12, comprising infusing the cold fluid at approximately one liter per minute or faster for two to four minutes.

14. The method of claim 13, wherein the temperature of the cold fluid is no more than five degrees Centigrade.

15. The method of claim 14, wherein the catheter includes a lower balloon disposed below the inferior mesenteric artery when the upper balloon is positioned at a location just above the renal arteries and celiac trunk, and the method comprises inflating the lower balloon to occlude flow of the cold fluid to aorta locations below the lower mesenteric artery, thereby ensuring that a majority of the cold fluid flows through the enteric vascular bed.

16. The method of claim 15, comprising positioning the catheter using ultrasound.

* * * * *